United States Patent
Schoen et al.

(10) Patent No.: US 7,820,801 B2
(45) Date of Patent: Oct. 26, 2010

(54) HIGHLY PURIFIED PROTEINASE K

(75) Inventors: Helmut Schoen, Penzberg (DE);
Guenter Guertler, Penzberg (DE);
Bernhard Rexer, Weilheim (DE);
Johann-Peter Thalhofer, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 248 days.

(21) Appl. No.: 11/536,866

(22) Filed: Sep. 29, 2006

(65) Prior Publication Data

US 2007/0179280 A1     Aug. 2, 2007

Related U.S. Application Data

(63) Continuation of application No. PCT/EP2005/003350, filed on Mar. 31, 2005.

(30) Foreign Application Priority Data

Apr. 2, 2004    (EP)    ................. 04008131

(51) Int. Cl.
*C08H 1/00*      (2006.01)
*C12N 9/50*      (2006.01)
*C12N 9/58*      (2006.01)
*C07K 14/00*     (2006.01)
*C07K 14/37*     (2006.01)

(52) U.S. Cl. .................. 530/420; 530/418; 530/350; 435/219; 435/223

(58) Field of Classification Search .............. 530/420, 530/418, 350; 435/219, 223
See application file for complete search history.

(56) References Cited

FOREIGN PATENT DOCUMENTS

WO    WO87 06939 A1  *  11/1987
WO    WO 02/064760 A2     8/2002

OTHER PUBLICATIONS

Luchi et al., "Molecular characteristics of canine cardiac myosin," Circulation Res 16:74-82, 1965.*
Betzel, C., Gourinath, S., Kumar, P., Kaur, P., Perbandt, M., Eschenburg, S., Singh, T., "Structure of a Serine Protease Proteinase K from *Tritirachium album limber* at 0.98 Å Resolution", Biochemistry 2001, 40, 3080-3088.
Ebeling, W., Hennrich, N., Klockow, M., Metz, H., Orth, H., and Lang, H., "Proteinase K from *Tritirachium album* Limber", Eur. J. Biochem. 47, 91-97 (1974).
"Proteinase K", Fermentas Catalog, Online, 2003.
Pähler, A., Banerjee, A., Dattagupta, J., Fujiwara, T., Lindner, K., Pal, G., Duck, S., Weber, G., Saenger, W., "Three-dimensional structure of fungal proteinase K reveals similarity to bacterial substilisin", The EMBO Journal vol. 3, No. 6, pp. 1311-1314, 1984.
Wiegers, J., Hilz, H., "A New Method Using 'Proteinase K' to Prevent mRNA Degradation During Isolation from HeLa Cells", Biochemical and Biophysical Research Communications, vol. 44, No. 2, 1971.
Wiegers, J., Hilz, H., "Rapid Isolation of Undegraded Polysomal RNA Without Pnenol", FEBS Letters 23, No. 1, 1972, pp. 77-82.

* cited by examiner

*Primary Examiner*—Karen Cochrane Carlson
*Assistant Examiner*—Rosanne Kosson
(74) *Attorney, Agent, or Firm*—Marilyn L. Amick; Roche Diagnostics Operations, Inc.

(57) ABSTRACT

A method for producing solid proteinase K which is insoluble in water and has high purity, the method comprising the steps of adding to an aqueous solution of proteinase K ammonium sulfate in an amount of 0.1 to 0.2 M per 5 minutes up to a final amount of 1.5 to 2 M after 1 hour, thereby precipitating the proteinase K as a solid, and isolating the solid proteinase K.

13 Claims, No Drawings

HIGHLY PURIFIED PROTEINASE K

RELATED APPLICATIONS

This application is a continuation of PCT/EP2005/003350 filed Mar. 31, 2005 and claims priority to EP 04008131.7 filed Apr. 2, 2004.

FIELD OF THE INVENTION

The present invention relates to a highly purified solid proteinase K preparation, a water-insoluble form of proteinase K, methods for its production, and use of a water-insoluble form of proteinase K.

BACKGROUND OF THE INVENTION

Proteinase K (EC 3.4.21.64) is a serine protease which can be isolated from the fungus *Tritirachium album limber* (Ebeling, W., et al., Eur. J. Biochem. 47 (1974) 91-97, and German Patent DE 19 65 281). Proteinase K is capable of digesting native keratin and remains active in the presence of low concentrations of SDS (sodium dodecyl sulfate). Therefore, proteinase K is very useful for the isolation of native RNAs in high yields (Wiegers, U., and Hilz, H., Biochem. Biophys. Res. Commun. 44 (1971) 513-519).

Proteinase K is also widely used in the field of PCR (polymerase chain reaction). In such methods there are used, in intermediate steps, certain enzymes such as restriction endonucleases, polymerases, and DNA modifying enzymes. It is often necessary to inactivate these enzymes before performing the next PCR step. Such inactivation is preferably performed by the use of proteinase K. It is therefore necessary that proteinase K is of high purity and is especially not contaminated with deoxyribonuclease, endonucleases, exonucleases, and DNA.

SUMMARY OF THE INVENTION

It was surprisingly found that time-controlled precipitation of proteinase K leads to a water-insoluble product characterized by a solubility of 0% in buffer A (10 mM Tris HCl, pH 7.5) or buffer B (5 mM Ca-acetate, pH 7.5) and by a solubility of 100% in buffer A containing 50% glycerol.

The invention therefore comprises a solid proteinase K preparation which is insoluble in water and obtainable by adding to an aqueous solution of proteinase K ammonium sulfate in an amount of 0.1 to 0.2 M per 5 minutes up to a final amount of 1.5 to 2 M after 1 hour, and isolating the precipitated proteinase K.

The invention also comprises a method for the preparation of proteinase K in a solid form by ammonium sulfate precipitation, characterized in that an aqueous solution of proteinase K is treated with a saturated aqueous solution of ammonium sulfate or with solid ammonium sulfate crystals under such conditions that proteinase K precipitates, characterized in that the ammonium sulfate is added to said aqueous solution of proteinase K in that ammonium sulfate concentration in said solution increases in an amount of 0.1 to 0.2 M per 5 minutes up to a final concentration of 1.5 M to 2 M after 1 hour and the formed proteinase K precipitate is isolated.

In a preferred embodiment of the invention, washing of the precipitate is performed with water or an aqueous buffer solution (pH 5.5 to 7.5), preferably with Tris or acetate buffer.

It is also preferred to isolate the proteinase K precipitate from the ammonium sulfate solution by centrifugation, preferably at 5,500 to 8,500 g.

Preferably, the proteinase K solution has a concentration of 20 mg/ml before ammonium sulfate is added.

Preferably, the added ammonium sulfate crystals are in powdered form. For example, ammonium sulfate crystals in powdered form that are commercially available in p.a. ("pro analysi") quality can be used. Such crystals are obtainable from suppliers of chemicals such as Mallinckrodt Baker.

It was surprisingly found that the solid form of proteinase K prepared according to the invention is not soluble in water in a considerable amount. Therefore, a further object of the invention is a preparation of a solid proteinase K preparation which is insoluble in water. However, the preparation is soluble in an aqueous solution containing 40 to 60% glycerol (w/v).

A further object of the invention is a method of solubilization of a solid preparation of proteinase K obtainable according to the invention by treating said preparation with an aqueous solution containing 40 to 60% glycerol (w/v).

The solid proteinase K can be in crystalline form, as precipitated, or in powdered form.

DETAILED DESCRIPTION OF THE INVENTION

The present invention provides a solid proteinase K preparation insoluble in water and obtainable by adding to an aqueous solution of proteinase K ammonium sulfate in an amount of 0.1 to 0.2 M per 5 minutes up to final amount of 1.5 to 2 M after 1 hour, and isolating the precipitated proteinase K.

The precipitation of proteins such as proteinase K by the use of ammonium sulfate is well-known in the state of the art. It is a general method for protein separation and purification. The method is commonly known as salting-out. Ammonium sulfate has been the most widely used salt for such a method because of its high solubility. According to the state of the art, a saturated salt solution or powdered salt crystals are added to the protein mixture to bring up the salt concentration of the mixture.

The present invention provides a method for the preparation of proteinase K in a solid form by ammonium sulfate precipitation, characterized in that an aqueous solution of proteinase K is treated with a saturated aqueous solution of ammonium sulfate or with solid ammonium sulfate crystals under such conditions that proteinase K precipitates, characterized in that ammonium sulfate is added to said aqueous solution of proteinase K such that the ammonium sulfate concentration in said solution increases in an amount of 0.1 M to 0.2 M per 5 minutes up to a final concentration of 1.5 M to 2 M after 1 hour, and the formed proteinase K precipitate is isolated.

Usually, while stirring, saturated ammonium sulfate solution is dropwise added to the protein solution until a precipitate starts to form. Usually, protein precipitation will require 15 to 20 minutes up to about an hour to equilibrate. After the precipitation is performed, the mixture is centrifuged, usually at about 10,000 g for 15 minutes, and the precipitate is collected. Usually, ammonium sulfate precipitation is performed at a temperature between 0° C. and 40° C. According to the invention, it is preferred to work at about 4° C. to 8° C.

During ammonium sulfate precipitation, the pH value is preferably about pH 7.5. After precipitation, centrifugation, and washing with water, the solid proteinase K preparation can be either stored or dissolved in an aqueous glycerol solution, Solubilization is preferably performed by dialysis against such a glycerol-containing aqueous solution.

By the addition of ammonium sulfate, either in crystals or as a separate aqueous solution, the volume of the solution does not increase in a considerable amount. If ammonium sulfate is added as a separate aqueous solution, the volume increases usually by about 5%.

According to the invention, it is possible to produce water-insoluble proteinase K according to the invention in every desired amount, e.g. from 1 mg or more to preferably up to 500 g or more.

Water-insoluble proteinase K crystals according to the invention can be washed using a buffer containing salts dissolved in water or with pure water. Water-soluble impurities are thereby removed from the water-insoluble proteinase K. The washing step can be repeated. Therefore, another embodiment of the invention is a method for the purification of proteinase K comprising the steps of (a) providing a solid proteinase K preparation insoluble in water and obtainable by adding to an aqueous solution of proteinase K ammonium sulfate in an amount of 0.1 to 0.2 M per 5 minutes up to a final amount of 1.5 to 2 M after 1 hour and isolating the precipitated proteinase K; (b) resuspending the precipitated proteinase K of step (a) in water or an aqueous buffer solution (pH 5.5 to 7.5); and (c) isolating the solid proteinase K of step (b). It is preferred that the aqueous buffer contains a buffer salt. Preferably, the buffer salt is a Tris salt. It is also preferred that the buffer is an acetate buffer. A preferred acetate buffer is Ca acetate buffer.

Crystallization of proteinase K is known in the state of the art in relation to X-ray cyrstallographic studies, e.g., by Pähler, A., EMBO J. 3 (1984)1311-1314 and Betzel, C., et al., Biochemistry 40 (2001) 3080-3088. However, such proteinase K crystals are prepared according to the usual methods for the production of X-ray crystals, which are cryo-cooling or microdialysis. Such crystals are not further purified and used as they are for X-ray investigations. In addition, such crystallization methods are not useful for the production of large amounts of proteinase K crystals of high purity quality.

The present invention further provides a method for the solubilization of a solid form of proteinase K obtainable according to a method of the invention, that is to say, obtainable by adding to an aqueous solution of proteinase K ammonium sulfate in an amount of 0.1 to 0.2 M per 5 minutes up to a final amount of 1.5 to 2 M after 1 hour and isolating the precipitated proteinase K, characterized in that solubilization is performed by adding an aqueous solution of glycerol at a concentration of 40% to 60% (w/v).

Due to its insolubility in water, the solid proteinase K preparation according to the invention can be used for in situ solubilization in a reagent solution instead of adding a proteinase K solution. Therefore, a further object of the invention is a method of inactivating a protein in a device containing said protein in an aqueous solution. Solid proteinase K according to the invention and glycerol are added in amounts such that the proteinase K is dissolved and the protein is inactivated. Preferably the final concentration of glycerol is between 45% and 55%. Inactivation means that the protein shows no detectable characteristic activity like polymerase or nuclease activity. Preferably the protein is a polymerase, deoxyribonuclease, endonuclease, or exonuclease. The amount of the protein is preferably between 14 and 20 mg/ml.

The following examples and references are provided to aid the understanding of the present invention, the true scope of which is set forth in the appended claims. It is understood that modifications can be made in the procedures set forth without departing from the spirit of the invention.

SPECIFIC EMBODIMENTS

Example 1

Crystallization of Dissolved Proteinase K

Buffer I consisting of 5 mM $CaCl_2$, 5 mM Ca acetate, 1 mM EDTA, 10 mM Tris HCl, pH 7.5, in water, was provided. Buffer I was cooled to a temperature between 4° C. and 8° C. Commercially available proteinase K (EC 3.4.21.14d) from *Tritirachium album* was provided as a lyophilisate. The lyophilisate was dissolved in Buffer I to result in a protein concentration of 19-20 mg/ml. To this end, the lyophilisate was added slowly to the buffer while stirring. The buffer was stirred until the lyophilisate had dissolved completely. The pH of the mixture was monitored and re-adjusted, if necessary, to the value of pH 7.5 using HCl.

Subsequently, solid powdered ammonium sulfate salt crystals were added slowly and continuously to the mixture. The rate of adding ammonium sulfate crystals to the mixture was adjusted such that within 1 h the ammonium sulfate concentration in the mixture was brought up to 1.8 M (290 mg/ml). While adding ammonium sulfate to the mixture, the mixture was stirred. Stirring was continued for 1 h when the concentration of ammonium sulfate was 1.8 M.

The precipitate portion, that is to say, the crystallized matter of the resulting suspension, was sedimented by centrifugation. The supernatant was removed.

Example 2

Washing of Proteinase K Crystals

The crystals obtained by the procedure of Example 1 were resuspended in Buffer I at a temperature between 4° C. and 8° C. The volume in which the crystals were resuspended was about the same as the volume of the mixture of Example 1. A smaller volume is also possible. The crystals were subsequently sedimented by centrifugation. The supernatant was removed.

Alternatively, the crystals obtained by the procedure of Example 1 were resuspended in water, at a temperature between 4° C. and 8° C. The volume in which the crystals were resuspended was about the same as the volume of the mixture of Example 1. A smaller volume is also possible. The crystals were subsequently sedimented by centrifugation. The supernatant was removed.

Example 3

Dissolving Proteinase K crystals

Buffer II consisting of 5 mM $CaCl_2$, 5 mM Ca acetate, 1 mM EDTA, 10 mM Tris HCl, pH 7.5, and 50% glycerol in water, was provided. Proteinase K crystals were obtained by the procedure of Example 1 or Example 2. Crystals were resuspended in an aliquot of Buffer I. The suspension was transferred into dialysis tubes and dialyzed against Buffer II.

Alternatively, an amount of Buffer II was added to crystals obtained by the procedure of Example 1 or the procedure of Example 2.

Example 4

Enzymatic Activity

As described in Example 1, proteinase K lyophilisate was dissolved in a volume of Buffer I at a final concentration of 19-20 mg/ml. Before adding ammonium sulfate salt, a sample was taken from the solution, and proteolytic activity was measured as activity per volume. Proteolytic activity was determined using hemoglobin as a substrate.

After the sedimentation step, the proteolytic activity was determined in the supernatant. The sediment comprising the proteinase K crystals was washed three times with each washing step comprising resuspending the sediment in water or in Buffer I and centrifuging the suspension. The volume of liquid in which the crystals were resuspended was equal to the volume of Buffer I in which the lyophilisate had been dissolved in the beginning. After each centrifugation step, a sample was taken from the supernatant, and the proteolytic activity in the supernatant was determined. After the last washing step, the proteinase K crystals were dissolved in a volume of Buffer II which equaled the volume of Buffer I in which the lyophilisate had been dissolved (see above). During this step, the crystals dissolved completely, and a clear solution was obtained. Again, the proteolytic activity was determined.

Table 1 summarizes the proteolytic activities which were detected in the samples as given above. Activity per volume is given for each sample relative to the activity per volume resulting from the dissolved lyophilisate in Buffer I.

TABLE I

| Proteinase K lyophilisate dissolved in Buffer 1 | Supernatant following precipitation with ammonium sulfate | Supernatant after 1st washing step (water) | Supernatant after 2nd washing step (water) | Supernatant after 3rd washing step (water) | Solution of proteinase K crystals after 3rd washing step |
|---|---|---|---|---|---|
| 100% | 2%-5% | 3%-5% | 1%-3% | not detectable | 85%-90% |

What is claimed is:

1. A method for producing solid proteinase K which is insoluble in water, the method comprising tile steps of:
    adding to an aqueous solution of proteinase K ammonium sulfate in an amount of 0.1 to 0.2 M per 5 minutes up to a final amount of 1.5 M to 2 M after 1 hour, thereby precipitating the proteinase K as a solid,
    resuspending the solid proteinase K in a buffer comprising Tris and calcium acetate, isolating the solid proteinase K,
    washing the solid proteinase K with an aqueous buffer or water to yield solid proteinase K and a supernatant, and measuring proteinase K activity in the supernatant, wherein the washing step is repeated until no proteinase K activity is measurably detected in the supernatant.

2. The method of claim 1 wherein the added ammonium sulfate is in a form selected from the group consisting of a saturated aqueous solution and powered crystals.

3. The method of claim 1 wherein the step of adding the ammonium sulfate is carried out at a temperature of about 4° C. to 8° C.

4. The method of claim 1 wherein the aqueous solution of proteinase K has a concentration of about 20 mg/dl proteinase K.

5. A method for the purification of proteinase K comprising the steps of:
    adding to an aqueous solution of proteinase K ammonium sulfate in an amount of 0.1 to 0.2 M per 5 minutes up to a final amount of 1.5 M to 2 M after 1 hour, thereby precipitating the proteinase K as a solid,
    resuspending the solid proteinase K in a buffer comprising Tris and calcium acetate, isolating the solid proteinase K,
    resuspending the isolated solid proteinase K in water or an aqueous buffer solution, and isolating the resuspended proteinase K from a supernatant, wherein proteinase K activity is not measurably detected in the supernatant.

6. The method of claim 5 wherein the added ammonium sulfate is in a form selected from the group consisting of a saturated aqueous solution and powered crystals.

7. The method of claim 5 wherein the step of adding the ammonium sulfate is carried out at a temperature of about 4° C. to 8° C.

8. The method of claim 5 wherein the aqueous solution of proteinase K has a concentration of about 20 mg/dl proteinase K.

9. A method for producing solubilized proteinase K comprising the steps of:
    adding to an aqueous solution of proteinase K ammonium sulfate in an amount of 0.1 to 0.2 M per 5 minutes up to a final amount of 1.5 to 2 M after 1 hour, thereby precipitating the proteinase K as a solid,
    resuspending the solid proteinase K in a buffer comprising Tris and calcium acetate, isolating the solid proteinase K wherein the solid proteinase K is insoluble in water, and
    adding to the isolated proteinase K an aqueous solution of glycerol at a concentration of 40% to 60% (w/v), thereby solubilizing the proteinase K.

10. The method of claim 9 wherein the added ammonium sulfate is in a form selected from the group consisting of a saturated aqueous solution and powered crystals.

11. The method of claim 9 wherein the step of adding the ammonium sulfate is carried out at a temperature of about 4° C. to 8° C.

12. The method of claim 9 wherein the aqueous solution of proteinase K has a concentration of about 20 mg/dl proteinase K.

13. The method of claim 1 wherein no proteinase activity is detectably measured after repeating the washing step three times.

* * * * *